(12) United States Patent
Khayrallah et al.

(10) Patent No.: US 11,072,579 B2
(45) Date of Patent: *Jul. 27, 2021

(54) TREATMENT OF CATAPLEXY

(71) Applicants: Jazz Pharmaceuticals International III Limited, Hamilton (BM); SK Biopharmaceuticals Co., Ltd., Seongnam-si (KR)

(72) Inventors: Moise A. Khayrallah, Morrisville, NC (US); Gary Bream, Cary, NC (US); Stephen E. Butts, Holly Springs, NC (US)

(73) Assignees: Jazz Pharmaceuticals Ireland Limited, Dublin (IE); SK Biopharmaceuticals Co., Ltd., Seongnam-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/359,446

(22) Filed: Mar. 20, 2019

(65) Prior Publication Data
US 2019/0218174 A1    Jul. 18, 2019

Related U.S. Application Data

(63) Continuation of application No. 15/419,133, filed on Jan. 30, 2017, now Pat. No. 10,259,780, which is a continuation of application No. 15/149,478, filed on May 9, 2016, now Pat. No. 9,585,863, which is a continuation of application No. 14/205,423, filed on Mar. 12, 2014, now Pat. No. 9,359,290.

(60) Provisional application No. 61/778,998, filed on Mar. 13, 2013.

(51) Int. Cl.

| A61K 31/27 | (2006.01) |
|---|---|
| C07C 271/02 | (2006.01) |
| C07C 271/00 | (2006.01) |
| A61K 9/00 | (2006.01) |
| A61K 31/325 | (2006.01) |
| A61K 45/06 | (2006.01) |
| A61K 9/20 | (2006.01) |

(52) U.S. Cl.
CPC .......... *C07C 271/02* (2013.01); *A61K 9/0053* (2013.01); *A61K 9/20* (2013.01); *A61K 31/27* (2013.01); *A61K 31/325* (2013.01); *A61K 45/06* (2013.01); *C07C 271/00* (2013.01)

(58) Field of Classification Search
None
See application file for complete search history.

(56) References Cited

U.S. PATENT DOCUMENTS

| 5,705,640 | A | 1/1998 | Choi et al. |
|---|---|---|---|
| 5,756,817 | A | 5/1998 | Choi et al. |
| 5,955,499 | A | 9/1999 | Choi et al. |
| 6,140,532 | A | 10/2000 | Choi et al. |
| 6,204,245 | B1 | 3/2001 | Siegel et al. |
| 8,232,315 | B2 | 7/2012 | Lee et al. |
| 8,440,715 | B2 | 5/2013 | Ahnaou et al. |
| 8,552,060 | B2 | 10/2013 | Palumbo et al. |
| 8,623,913 | B2 | 1/2014 | Melnick et al. |
| 8,729,120 | B2 | 5/2014 | Sporn |
| 8,741,950 | B2 | 6/2014 | Khayrallah et al. |
| 2005/0080268 | A1 | 4/2005 | Choi et al. |
| 2008/0039529 | A1 | 2/2008 | Sporn |
| 2008/0090902 | A1 | 4/2008 | Pandey et al. |
| 2009/0312416 | A1 | 12/2009 | Ahnaou et al. |
| 2012/0004300 | A1 | 1/2012 | Lee et al. |
| 2012/0245226 | A1 | 9/2012 | Lee et al. |
| 2012/0252892 | A1 | 10/2012 | Lee et al. |
| 2013/0137764 | A1 | 5/2013 | Ahnaou et al. |
| 2014/0243406 | A1 | 8/2014 | Khayrallah et al. |

FOREIGN PATENT DOCUMENTS

| CN | 1656072 | 8/2005 |
|---|---|---|
| CN | 1960981 | 5/2007 |
| CN | 101217949 | 7/2008 |
| EP | 0633023 | 3/1995 |
| JP | 2008512386 | 4/2008 |
| JP | 2008545795 | 12/2008 |
| JP | 2009544673 | 12/2009 |
| JP | 2010510175 | 4/2010 |
| WO | 96/07637 | 3/1996 |
| WO | 96/24577 | 8/1996 |
| WO | 96/32375 | 10/1996 |
| WO | 98/15526 | 4/1998 |
| WO | 98/17636 | 4/1998 |
| WO | 2006/050037 | 5/2006 |
| WO | 2006/133393 | 12/2006 |
| WO | 2007/018496 | 2/2007 |
| WO | 2008/048801 | 4/2008 |
| WO | 2011/005473 | 1/2011 |

OTHER PUBLICATIONS

Database Registry Chemical Abstracts Service, Columbus, Ohio, Accession No. RN 178429-64-6. Entered STN: Jul. 17, 1996.*
Office Action corresponding to Mexican Application No. MX/A/2015/012644 dated Jul. 26, 2019.
Office Action corresponding to Brazilian Application No. BR112015022197-1 dated Sep. 17, 2019.
U.S. Appl. No. 15/149,478; office action dated Jul. 11, 2016.
Examination Report corresponding to European Application No. 14778088.6 dated Jan. 22, 2019.
Examination Report corresponding to Indian Application No. 9236/DELNP/2015 dated Dec. 14, 2018.
Extended European Search Report corresponding to European Application No. 14778088.6 dated Sep. 14, 2016.

(Continued)

*Primary Examiner* — Samantha L Shterengarts
(74) *Attorney, Agent, or Firm* — Myers Bigel, P.A.

(57) ABSTRACT

The present invention relates to a method of treating cataplexy in a subject in need thereof, comprising administering to the subject a therapeutically effective amount of certain carbamate compounds.

12 Claims, No Drawings

(56) References Cited

OTHER PUBLICATIONS

Houghton et al. "Pharmacotherapy for cataplexy", Sleep Medicine Reviews 8:355-366 (2004).
Invitation to Response to Written Opinion corresponding to Singapore Application No. 11201507121R dated Dec. 19, 2016.
Invitation to Response Written Opinion corresponding to Singapore Application No. 11201507121R dated Jun. 22, 2016.
Invitation to Response to Written Opinion corresponding to Singapore Application No. 11201507121R dated Nov. 5, 2018.
Invitation to Response to Written Opinion corresponding to Singapore Application No. 11201507121R dated Oct. 23, 2017.
Morgenthaler, T.I. et al (2009), Practice Parameters for the Treatment of Narcolepsy and other Hypersomnia of Central Origin an American Academy of Sleep Medicine Report: An American Academy of Sleepy Medicine Report. Sleep, 30 (12), Dec. 1, 2007 (Dec. 1, 2007), pp. 1705-1711.
Office Action corresponding to Chinese Application No. 201480027152.9 dated Dec. 5, 2016.
Office Action corresponding to Chinese Application No. 201480027152.9 dated Jun. 8, 2018.
Office Action corresponding to Chinese Application No. 201480027152.9 dated Nov. 29, 2017.
Office Action corresponding to Japanese Application No. 2016-501395 dated Aug. 23, 2018.
Office Action corresponding to Japanese Application No. 2016-501395 dated Dec. 12, 2017.
Office Action corresponding to Philippine Application No. 1/2015/502075 dated Aug. 7, 2018.
Office Action corresponding Philippine Application No. 1/2015/502075 dated Nov. 12, 2018.
Office Action corresponding to Russian Application No. 2015143610 dated Mar. 20, 2018.
Office Action corresponding to Russian Application No. 2015143610 dated Sep. 25, 2018.
Office Action corresponding to Taiwan Application No. 103108612 dated Feb. 23, 2018.
Office Action corresponding to Taiwan Application No. 103108612 dated Aug. 21, 2017.
Office Action corresponding to Thai Application No. 1501005211 dated Mar. 19, 2017.
Office Action corresponding to Thai Application No. 1501005211 dated Oct. 15, 2017.
Office Action corresponding to Vietnamese Application No. 1-2015-03875 dated Aug. 29, 2017.
Amsterdam et al. "A single-site, double-blind, placebo-controlled, dose-ranging study of YKP10A—a putative, new antidepressant", Progress in Neuro-Psychopharmacol. Biol. Psychiatry 26:1333-1338 (2002).
Gordon et al. "Abstracts of he 28th Annual Meeting", Soc. NeuroSci. 24:1490-1491 (1998).
Hasan et al., "How to Keep the Brain Awake? The Complex Molecular Pharmacogenetics of Wake Promotion," Neuropsychopharmacology 34:1625-1640 (2009).
Notification of the International Search Report and the Written Opinion of the International Searching Authority, or the Declaration corresponding to International Application No. PCT/US2014/023969 dated Aug. 21, 2014.
Bogan et al., "Effect of oral JZP-110 (ADX-N05) treatment on wakefulness and sleepiness in adults with narcolepsy," Sleep Med. 16:1102-1108 (2015).
Sullivan et al., "Emerging drugs for common conditions of sleepiness: obstructive sleep apnea and narcolepsy," Exp. Opin. Emerging Drugs 20:571-582 (2015).
International Preliminary Report on Patentability corresponding to International Application No. PCT/US2014/023969 dated Sep. 24, 2015.
Examination Report corresponding to Australian Application No. 2014248849 dated Sep. 7, 2017.
Office Action corresponding to Canadian Application No. 2,905,457 dated Mar. 6, 2020.
Office Action corresponding to Indian Application No. 201918026927 dated Mar. 11, 2020.
Office Action corresponding to Russian Application No. 2019114940 dated Apr. 30, 2020.
Phenprobamate, Wikipedia, https://en.wikipedia.org/wiki/Phenprobamate, last edited Apr. 2, 2016, accessed Sep. 24, 2019.
Office Action corresponding to Russian Application No. 2019114940 dated Dec. 25, 2019.
"Narcolepsy with cataplexy", Lancet, vol. 369, pp. 499-511 (Feb. 10, 2007).
"Office Action corresponding to Korean Application No. 10-2015-7027978 dated Sep. 1, 2020".
"Office Action corresponding to Mexican Application No. MX/A/2015/012644 dated Aug. 14, 2020".

* cited by examiner

TREATMENT OF CATAPLEXY

STATEMENT OF PRIORITY

This application is a continuation of and claims priority to U.S. patent application Ser. No. 15/419,133, filed Jan. 30, 2017which is a continuation of and claims priority to U.S. patent application Ser. No. 15/149,478, filed May 9, 2016, now U.S. Pat. No. 9,585,863, which is a continuation of and claims priority to U.S. patent application Ser. No. 14/205,423, filed Mar. 12, 2014, now U.S. Pat. No. 9,359,290, which claims the benefit, under 35 U.S.C. § 119(e), of U.S. Provisional Application No. 61/778,998, filed Mar. 13, 2013, the entire contents of each of which are incorporated by reference herein.

FIELD OF THE INVENTION

The present invention relates to a method of treating cataplexy in a subject in need thereof, comprising administering to the subject a therapeutically effective amount of certain carbamate compounds.

BACKGROUND

Cataplexy is a sudden and transient episode of loss of muscle tone, often triggered by emotions such as laughter, fear, anger, frustration, annoyance, nervousness, embarrassment, and sadness. The sudden loss of muscle tone in cataplexy is similar to rapid eye movement (REM)-associated muscle atonia during sleep, but it is occurring during wakefulness. A cataplectic attack is sudden in onset and is localized to a specific muscle group or parts of the body. The subject is lucid during this attack; consciousness is always maintained at the onset of cataplexy. A full-blown attack may occur and results in complete muscle paralysis with postural collapse and possible injury. However, most often patients with postural collapse have the capability to avoid injury because the fall is slow and progressive. The more commonly limited cataplectic attacks involve the head and face, neck, upper limb, and more rarely lower limb known as "knee buckling." Attacks can last from a few seconds up to ten minutes, and may occur up to several times per week. In some patients, status cataplecticus, or periods of repetitive loss of muscle tone, occurs and can last for hours or days.

Cataplexy is a rare disease (prevalence of fewer than 5 per 10,000 in the community), but affects roughly 70% of people who have narcolepsy. However, in some cases, cataplexy occurs without the co-occurrence of narcolepsy. Furthermore, upwards of 30% of patients with narcolepsy may never experience cataplexy. The exact cause of cataplexy is unknown, but the condition is strongly linked to experiencing intense emotions and reduced levels of the neurotransmitter hypocretin. Cataplexy is considered secondary when it is due to specific lesions in the brain that cause a depletion of the hypocretin neurotransmitter. Cataplexy can also be present as a side effect of discontinuation of certain drugs, such as selective serotonin re-uptake inhibitor (SSRI) antidepressants.

Cataplexy, whether associated with narcolepsy or other causes, is disabling and potentially dangerous. Regardless of cause, cataplexy is linked to a variety of transportation and industrial accidents and cause decreased job performance and considerable subjective distress. A therapeutic agent that reduces or eliminates cataplexy would have important implications not only for individual patients, but also for public health and safety.

SUMMARY OF EMBODIMENTS OF THE INVENTION

The present invention is directed to a method of treating cataplexy in a subject in need thereof, comprising administering to the subject a therapeutically effective amount of a compound of Formula I:

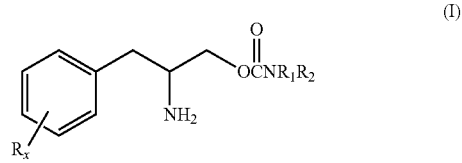

or a pharmaceutically acceptable salt or ester thereof, wherein R is a member selected from the group consisting of alkyl of 1 to 8 carbon atoms, halogen, alkoxy containing 1 to 3 carbon atoms, nitro, hydroxy, trifluoromethyl, and thioalkoxy containing 1 to 3 carbon atoms; x is an integer of 0 to 3, with the proviso that R may be the same or different when x is 2 or 3; $R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; or $R_1$ and $R_2$ can be joined to form a 5 to 7-membered heterocycle optionally substituted with a member selected from the group consisting of alkyl and aryl groups, wherein the heterocycle can comprise 1 to 2 nitrogen atoms and 0 to 1 oxygen atom, wherein the nitrogen atoms are not directly connected with each other or with the oxygen atom.

Embodiments of the invention include a method of treating cataplexy in a subject in need thereof, comprising the step of administering to the subject a therapeutically effective amount of an enantiomer of Formula I substantially free of other enantiomers or an enantiomeric mixture wherein one enantiomer of Formula I predominates.

In some embodiments, the compound of Formula I is a compound of Formula Ia:

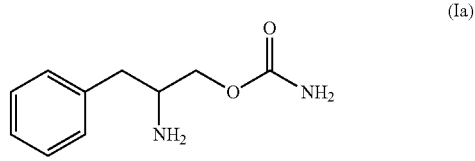 [SMILES: NC(=O)OCC(N)Cc1ccccc1]

or a pharmaceutically acceptable salt or ester thereof.

In some embodiments, the compound of Formula I is a compound of Formula Ib:

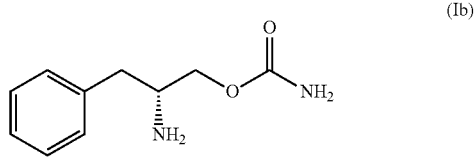 [SMILES: NC(=O)OC[C@H](N)Cc1ccccc1]

or a pharmaceutically acceptable salt or ester thereof. This compound is named (R)-(beta-amino-benzenepropyl) carbamate or O-carbamoyl-(D)-phenylalaninol and has alternatively been called ADX-N05, SKL-N05, YKP10A, and R228060.

Embodiments of the invention include the use, for the preparation of a medicament for the treatment of cataplexy, of an enantiomer of Formula I substantially free of other enantiomers or an enantiomeric mixture wherein one enantiomer of Formula I predominates.

DETAILED DESCRIPTION OF EMBODIMENTS OF THE INVENTION

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Definitions

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a compound) and the like, is meant to encompass variations of ±20%, ±10%, ±5%, ±1%, ±0.5%, or even ±0.1% of the specified amount.

The terms "comprise," "comprises," and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim or the description of this invention is not intended to be interpreted to be equivalent to "comprising."

As used herein, the terms "increase," "increases," "increased," "increasing," and similar terms indicate an elevation of at least about 25%, 50%, 75%, 100%, 150%, 200%, 300%, 400%, 500% or more.

As used herein, the terms "reduce," "reduces," "reduced," "reduction," and similar terms mean a decrease of at least about 5%, 10%, 15%, 20%, 25%, 35%, 50%, 75%, 80%, 85%, 90%, 95%, 97% or more. In particular embodiments, the reduction results in no or essentially no (i.e., an insignificant amount, e.g., less than about 10% or even 5%) detectable activity or amount.

"Effective amount" as used herein refers to an amount of a compound, composition and/or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of skill in the art by reference to the pertinent texts and literature and/or by using routine experimentation.

By the term "treat," "treating," or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. With respect to cataplexy, the term refers to a decrease in the number of attacks, a decrease in the length of attacks, and/or a decrease in the severity of attacks. For example, treatment may produce a decrease in the number of cataplectic events per week of at least about 20%, e.g., at least about 30%, 40%, 50%, 60%, 70%, 80%, or more.

A "treatment effective" amount as used herein is an amount that is sufficient to treat (as defined herein) the subject. Those skilled in the art will appreciate that the therapeutic effects need not be complete or curative, as long as some benefit is provided to the subject.

A "subject" of the invention includes any animal that has or is suspected of having cataplexy. Such a subject is generally a mammalian subject (e.g., a laboratory animal such as a rat, mouse, guinea pig, rabbit, primate, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. In certain embodiments, a subject of the invention can be a subject known to have or believed to have cataplexy. A subject of the invention can be a subject known or believed to be at risk of developing cataplexy. Alternatively, a subject according to the invention can also include a subject not previously known or suspected to have cataplexy. In embodiments of the invention the subject has or is suspected of having narcolepsy. Subjects include males and/or females of any age, including neonates, juvenile, mature and geriatric subjects.

A "subject in need" of the methods of the invention can be a subject known to have cataplexy, suspected of having cataplexy, or having an increased risk of developing cataplexy. In some embodiments, a "subject in need" is one that has moderate or severe cataplexy, e.g., a subject having 3 or more cataplectic events a week, e.g., 4, 5, 6, 7, 8, 9, or 10 or more cataplectic events a week.

The term "pharmaceutically acceptable salts or esters" shall mean non-toxic salts or esters of the compounds employed in this invention which are generally prepared by reacting the free acid with a suitable organic or inorganic base or the free base with a suitable organic or inorganic acid. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamoate, palmitate, panthothenate, phosphate/diphosphate, polygalacturonate, potassium, salicylate, sodium, stearate, subacetate, succinate, tannate, tartrate, teoclate, tosylate, triethiodide, and valerate.

As used herein the term "concomitant administration" or "combination administration" of a compound, therapeutic agent or known drug with a compound of the present invention means administration of a known medication or drug and, in addition, the one or more compounds of the invention at such time that both the known drug and the compound will have a therapeutic effect. In some cases this therapeutic effect will be synergistic. Such concomitant administration can involve concurrent (i.e., at the same time), prior, or subsequent administration of the known drug with respect to the administration of a compound of the present invention. A person of skill in the art, would have no difficulty determining the appropriate timing, sequence and dosages of administration for particular drugs and compounds of the present invention.

In addition, in some embodiments, the compounds of this invention will be used, either alone or in combination with each other or in combination with one or more other therapeutic medications as described above, or their salts or esters, for manufacturing a medicament for the purpose of providing treatment for cataplexy to a patient or subject in need thereof.

The present invention is based in part on the discovery that phenylalkylamino carbamates of Formula I have novel and unique pharmacological properties. These compounds have been shown to have a beneficial effect on DREM and cataplexy. Although the precise mechanism of action is not completely understood, it is believed that these compounds do not work by the same mechanisms as most other known stimulant drugs in producing their effects. For this reason the compounds of Formula I are especially suitable for use as treatment for cataplexy. Thus, these compounds can be safely used for this purpose to provide effective treatment of cataplexy regardless of the precise etiology of the disorder.

One aspect of the invention relates to a method of treating cataplexy in a subject in need thereof, comprising administering to the subject a therapeutically effective amount of a compound of Formula I:

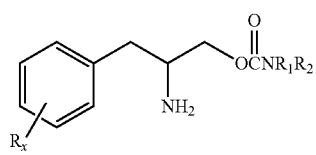

(I)

or a pharmaceutically acceptable salt or ester thereof; wherein R is a member selected from the group consisting of lower alkyl of 1 to 8 carbon atoms, halogen, alkoxy containing 1 to 3 carbon atoms, nitro, hydroxy, trifluoromethyl, and thioalkoxy containing 1 to 3 carbon atoms; x is an integer of 0 to 3, with the proviso that R may be the same or different when x is 2 or 3; $R_1$ and $R_2$ are independently selected from the group consisting of hydrogen, lower alkyl of 1 to 8 carbon atoms, aryl, arylalkyl, cycloalkyl of 3 to 7 carbon atoms; or $R_1$ and $R_2$ can be joined to form a 5 to 7-membered heterocycle optionally substituted with a member selected from the group consisting of alkyl, and aryl groups, wherein the heterocycle can comprise 1 to 2 nitrogen atoms and 0 to 1 oxygen atom, wherein the nitrogen atoms are not directly connected with each other or with the oxygen atom.

It is understood that substituents and substitution patterns on the compounds of the present invention can be selected by one of skill in the art to provide compounds that are chemically stable and that can be readily synthesized by techniques known in the art as well as the methods provided herein.

In one embodiment, the compound of Formula I is a compound of Formula Ia:

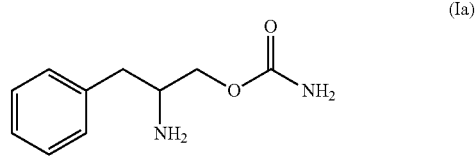 [SMILES: NC(=O)OCC(N)Cc1ccccc1]

(Ia)

or a pharmaceutically acceptable salt or ester thereof.

In one embodiment the compound of Formula I is the (D) enantiomer wherein $R_1$ and $R_2$ are hydrogen and x is 0 (compound Ib).

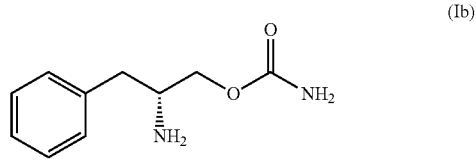 [SMILES: NC(=O)OC[C@H](N)Cc1ccccc1]

(Ib)

or a pharmaceutically acceptable salt or ester thereof. This compound is the (R) enantiomer, if named by structure and is therefore (R)-(beta-amino-benzenepropyl) carbamate. This compound is the dextrorotary enantiomer and can therefore also be named O-carbamoyl-(D)-phenylalaninol. The compound is also named ADX-N05. These names may be used interchangeably in this specification.

The present invention includes the use of isolated enantiomers of the compound of Formula I (e.g., compounds of Formula Ia or Ib). In one embodiment, a pharmaceutical composition comprising the isolated S-enantiomer of Formula I is used to provide treatment to a subject. In another embodiment, a pharmaceutical composition comprising the isolated R-enantiomer of Formula I is used to provide treatment to a subject.

The present invention also includes the use of mixtures of enantiomers of Formula I. In one aspect of the present invention, one enantiomer will predominate. An enantiomer that predominates in the mixture is one that is present in the mixture in an amount greater than any of the other enantiomers present in the mixture, e.g., in an amount greater than 50%. In one aspect, one enantiomer will predominate to the extent of 90% or to the extent of 91%, 92%, 93%, 94%, 95%, 96%, 97% or 98% or greater. In one embodiment, the enantiomer that predominates in a composition comprising a compound of Formula I is the S-enantiomer of Formula I.

The present invention provides methods of using enantiomers and enantiomeric mixtures of compounds represented by Formula I. A carbamate enantiomer of Formula I contains an asymmetric chiral carbon at the benzylic position, which is the second aliphatic carbon adjacent to the phenyl ring.

An enantiomer that is isolated is one that is substantially free of the corresponding enantiomer. Thus, an isolated enantiomer refers to a compound that is separated via separation techniques or prepared free of the corresponding enantiomer.

The term "substantially free," as used herein, means that the compound is made up of a significantly greater proportion of one enantiomer. In preferred embodiments, the compound includes at least about 90% by weight of one enantiomer. In other embodiments of the invention, the compound includes at least about 99% by weight of one enantiomer.

The compounds of Formula I can be synthesized by methods known to the skilled artisan. The salts and esters of the compounds of Formula I can be produced by treating the compound with a suitable mineral or organic acid (HX) in suitable solvent or by other means well known to those of skill in the art.

Details of reaction schemes for synthesizing compounds of Formula I as well as representative examples on the preparation of specific compounds have been described in U.S. Pat. Nos. 5,705,640, 5,756,817, 5,955,499, 6,140,532, all incorporated herein by reference in their entirety.

From Formula I it is evident that some of the compounds of the invention have at least one and possibly more asymmetric carbon atoms. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known in the art.

The compound may be administered to a subject by any conventional route of administration, including, but not limited to, oral, buccal, topical, systemic (e.g., transdermal, intranasal, or by suppository), or parenteral (e.g., intramuscular, subcutaneous, or intravenous injection.) Administration of the compounds directly to the nervous system can include, for example, administration to intracerebral, intraventricular, intracerebralventricular, intrathecal, intracisternal, intraspinal or peri-spinal routes of administration by delivery via intracranial or intravertebral needles or catheters with or without pump devices. Depending on the route of administration, compounds of Formula I can be constituted into any form. For example, forms suitable for oral administration include solid forms, such as pills, gelcaps, tablets, caplets, capsules, granules, and powders (each including immediate release, timed release and sustained release formulations). Forms suitable for oral administration also include liquid forms, such as solutions, syrups, elixirs, emulsions, and suspensions. In addition, forms useful for parenteral administration include sterile solutions, emulsions and suspensions.

In certain embodiments, pharmaceutical compositions of this invention comprise one or more compounds of Formula I or a salt or ester thereof without any pharmaceutical carriers or excipients. In other embodiments, pharmaceutical compositions of this invention comprise one or more compounds of formula I or a salt or ester thereof intimately admixed with a pharmaceutical carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the usual pharmaceutical carriers may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like.

Compositions can take the form of tablets, pills, capsules, semisolids, powders, sustained release formulations, solutions, suspensions, emulsions, syrups, elixirs, aerosols, or any other appropriate compositions; and comprise at least one compound of this invention, optionally in combination with at least one pharmaceutically acceptable excipient. Suitable excipients are well known to persons of ordinary skill in the art, and they, and the methods of formulating the compositions, can be found in such standard references as Alfonso A R: Remington's Pharmaceutical Sciences, 17th ed., Mack Publishing Company, Easton Pa., 1985, the disclosure of which is incorporated herein by reference in its entirety and for all purposes. Suitable liquid carriers, especially for injectable solutions, include water, aqueous saline solution, aqueous dextrose solution, and glycols.

The carbamate compounds can be provided as aqueous suspensions. Aqueous suspensions of the invention can contain a carbamate compound in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate).

The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions for use in the present methods can be formulated by suspending a carbamate compound in a vegetable oil, such as arachis oil, olive oil, sesame oil or coconut oil, or in a mineral oil such as liquid paraffin, or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93 (1997). The pharmaceutical formulations of the invention can also be in the form of oil-in-water emulsions. The oily phase can be a vegetable oil or a mineral oil, as described above, or a mixture of these.

Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations of the present invention suitable for parenteral administration, such as, for example, by intraarticular (in the joints), intravenous, intramuscular, intradermal, intraperitoneal, and subcutaneous routes, can include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter.

Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well-known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The concentration of a carbamate compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using suitable dispersing or wetting agents and suspending agents. The sterile injectable preparation can also be a sterile injectable solution or suspension in a nontoxic parenterally acceptable diluent or solvent, such as a solution of 1,3-butanediol. The formulations of commends can be presented in unit-dose or multi-dose sealed containers, such as ampoules and vials. Injection solutions and suspensions can be prepared from sterile powders, granules, and tablets of the kind previously described.

A carbamate compound suitable for use in the practice of this invention can be administered orally. The amount of a compound of the present invention in the composition can vary widely depending on the type of composition, size of a unit dosage, kind of excipients, and other factors well known to those of skill in the art. In general, the final composition can comprise, for example, from 0.000001 percent by weight (% w) to 100% w of the carbamate compound, e.g., 0.00001% w to 50% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. In other embodiments, pharmaceutical formulations for oral administration can be formulated without using any pharmaceutically acceptable carriers.

Formulations suitable for oral administration can consist of (a) liquid solutions, such as an effective amount of the pharmaceutical formulation suspended in a diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethyl-cellulose; and gums including arabic and tragacanth; as well as proteins such as gelatin and collagen.

If desired, disintegrating or solubilizing agents can be added, such as cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient that is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187 (1995); Tjwa, Ann. Allergy Asthma Immunol. 75:107 (1995)).

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug (e.g., mifepristone)-containing microspheres, which slowly release subcutaneously (see Rao, J. Biomater. Sci. Polym. Ed. 7:623 (1995); as biodegradable and injectable gel formulations (see, e.g., Gao, Pharm. Res. 12:857 (1995)); or, as microspheres for oral administration (see, e.g., Eyles, J. Pharm. Pharmacol. 49:669 (1997)). Both transdermal and intradermal routes afford constant delivery for weeks or months. Cachets can also be used in the delivery of the compounds of the present invention.

In another embodiment, the compounds of the present invention can be delivered by the use of liposomes which fuse with the cellular membrane or are endocytosed, i.e., by employing ligands attached to the liposome that bind to surface membrane protein receptors of the cell resulting in endocytosis. The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

By using liposomes, particularly where the liposome surface carries ligands specific for target cells, or are otherwise preferentially directed to a specific organ, one can focus the delivery of the carbamate compound into target cells in vivo (see, e.g., Al-Muhammed, J. Microencapsul. 13:293 (1996); Chonn, Curr. Opin. Biotechnol. 6:698 (1995); Ostro, Am. J. Hosp. Pharm. 46:1576 (1989)).

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

In certain embodiments the compositions are in unit dosage forms such as tablets, pills, capsules, powders, granules, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation.

Alternatively, the composition may be presented in a form suitable for once-weekly or once-monthly administration; for example, an insoluble salt of the active compound, such as the decanoate salt, may be adapted to provide a depot preparation for intramuscular injection.

The pharmaceutical compositions herein will contain, per dosage unit, e.g., tablet, capsule, powder, injection, teaspoonful, suppository and the like, an amount of the active ingredient necessary to deliver an effective dose as described above. For example, the pharmaceutical compositions herein can contain, per unit dosage unit, from about 10 to about 1000 mg of the active ingredient, e.g., from about 25 to about 600 mg of the active ingredient, e.g., from about 75 to about 400 mg of the active ingredient, e.g., about 25, 50, 75, 100, 125, 150, 175, 200, 225, 250, 275, 300, 325, 350, 375, 400, 425, 450, 475, 500, 525, 550, 575, or 600 mg or more or any range therein.

In some embodiments of the present invention, carbamate compounds suitable for use in the practice of this invention will be administered either singly or concomitantly with at least one or more other compounds or therapeutic agents, e.g., with other agents that treat cataplexy and/or other disorders or symptoms associated with cataplexy or narcolepsy (e.g., excessive daytime sleepiness, hypnagogic hallucinations, and sleep paralysis). Examples of therapeutic agents for treating cataplexy include, without limitation, antidepressants (e.g., tricyclics (such as clomiprimine, imipramine, and protriptyline) and selective serotonin reuptake inhibitors (such as fluoxetine, paroxetine, sertraline, citalopam)) and sodium oxybate (gamma-hydroxybutyrate [GHB]). Therapeutic agents for treating excessive daytime sleepiness and other symptoms of narcolepsy include, without limitation, amphetamines (such as dexamphetamine, methamphetamine, and methylphenidate), modafinil, armodafinil, atomoxetine, and selegiline. Sodium oxybate is the only medication known to improve both cataplexy and excessive daytime sleepiness.

The method includes the step of administering to a patient in need of treatment an effective amount of one of the carbamate compounds disclosed herein in combination with an effective amount of one or more other compounds or therapeutic agents that have the ability to provide advantageous combined effects such as the ability to augment the effects of the compounds of the invention.

Pharmaceutically acceptable salts and esters refers to salts and esters that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Pharmaceutically acceptable salts can also include acid addition salts formed from the reaction of amine moieties in the parent compound with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds. When there are two acidic groups present, a pharmaceutically acceptable salt or ester may be a mono-acid-mono-salt or ester or a di-salt or ester; and similarly where there are more than two acidic groups present, some or all of such groups can be salified or esterified.

Compounds named in this invention can be present in unsalified or unesterified form, or in salified and/or esterified form, and the naming of such compounds is intended to include both the original (unsalified and unesterified) compound and its pharmaceutically acceptable salts and esters. The present invention includes pharmaceutically acceptable salt and ester forms of Formula I. More than one crystal form of an enantiomer of Formula I can exist and as such are also included in the present invention.

A pharmaceutical composition of the invention can optionally contain, in addition to a carbamate compound, at least one other therapeutic agent useful in the treatment of cataplexy. For example the carbamate compounds of Formula I can be combined physically with other compounds in fixed dose combinations to simplify their administration.

Methods of formulating pharmaceutical compositions have been described in numerous publications such as Pharmaceutical Dosage Forms: Tablets. Second Edition. Revised and Expanded. Volumes 1-3, edited by Lieberman et al.; Pharmaceutical Dosage Forms: Parenteral Medications. Volumes 1-2, edited by Avis et al.; and Pharmaceutical Dosage Forms: Disperse Systems. Volumes 1-2, edited by Lieberman et al.; published by Marcel Dekker, Inc, the disclosure of each of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

The present invention provides methods of providing treatment for cataplexy in a mammal using carbamate compounds. The amount of the carbamate compound necessary to provide treatment for cataplexy is defined as a therapeutically or a pharmaceutically effective dose. The dosage schedule and amounts effective for this use, i.e., the dosing or dosage regimen will depend on a variety of factors including the stage of the disease, the patient's physical status, age and the like. In calculating the dosage regimen for a patient, the mode of administration is also taken into account.

A person of skill in the art will be able without undue experimentation, having regard to that skill and this disclosure, to determine a therapeutically effective amount of a particular substituted carbamate compound for practice of this invention (see, e.g., Lieberman, Pharmaceutical Dosage Forms (Vols. 1-3, 1992); Lloyd, 1999, The Art, Science and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

For treatment purposes, the compositions or compounds disclosed herein can be administered to the subject in a single bolus delivery, via continuous delivery over an extended time period, or in a repeated administration protocol (e.g., by an hourly, daily or weekly, repeated administration protocol). The pharmaceutical formulations of the present invention can be administered, for example, one or more times daily, 3 times per week, or weekly. In one embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to provide treatment for cataplexy. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays).

Using such models, only ordinary calculations and adjustments are typically required to determine an appropriate concentration and dose to administer a therapeutically effective amount of the biologically active agent(s) (e.g., amounts that are orally effective intranasally effective, transdermally effective, intravenously effective, or intramuscularly effective to elicit a desired response). The effective amount, however, may be varied depending upon the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

In an exemplary embodiment of the present invention, unit dosage forms of the compounds are prepared for standard administration regimens. In this way, the composition can be subdivided readily into smaller doses at the physician's direction. For example, unit dosages can be made up in packeted powders, vials or ampoules and preferably in capsule or tablet form.

Effective administration of the carbamate compounds of this invention can be, for example, at an oral or parenteral dose of from about 0.01 mg/kg/dose to about 150 mg/kg/dose. For example, administration can be from about 0.1/mg/kg/dose to about 25 mg/kg/dose, e.g., from about 0.2 to about 18 mg/kg/dose, e.g., from about 0.5 to about 10 mg/kg/dose. Therefore, the therapeutically effective amount of the active ingredient can be, for example, from about 1 mg/day to about 7000 mg/day for a subject having, for example, an average weight of 70 kg, e.g., from about 10 to about 2000 mg/day, e.g., from about 50 to about 600 mg/day, e.g., about 10, 25, 50, 75, 100, 125, 150, 175, 200, 225, 250, 275, 300, 325, 350, 375, 400, 425, 450, 475, 500, 525, 550, 575, or 600 mg/day or more or any range therein. In one embodiment, the compound of Formula I is administered in the form of a capsule at a dose of about 150 mg to about 300 mg without any excipients.

The methods of this invention also provide for kits for use in providing treatment for cataplexy. After a pharmaceutical composition comprising one or more carbamate compounds of this invention, with the possible addition of one or more other compounds of therapeutic benefit, has been formulated in a suitable carrier, it can be placed in an appropriate container and labeled for providing treatment for cataplexy. Additionally, another pharmaceutical comprising at least one other therapeutic agent can be placed in the container as well and labeled for treatment of the indicated disease. Such labeling can include, for example, instructions concerning the amount, frequency and method of administration of each pharmaceutical.

Embodiments according to the present invention are described in non-limiting examples below.

EXAMPLE 1

Clinical Trial With Narcolepsy Patients

A study of the safety and efficacy of ADX-N05 in the treatment of excessive daytime sleepiness in subjects with narcolepsy is carried out. The study includes an exploratory analysis of the potential efficacy of ADX-N05 in the subset of narcolepsy subjects in this study who also have cataplexy.

The study is a double-blind, flexible target-dose, placebo-controlled, multi-center, randomized, parallel-group, study. Following the successful completion of a Screening Phase and Baseline Phase, subjects are randomized to one of two treatment groups and receive ADX-N05 or placebo over a treatment period of 12 weeks (Treatment Group #1: Weeks 1-4: ADX-N05 150 mg/day; Weeks 5-12: ADX-N05 300 mg/day; Treatment Group #2: Weeks 1-12: Placebo) as shown in Table 1. Approximately 90 subjects (45 per treatment group) are enrolled into the study. Each subject completes Screening, Baseline, Treatment, and Follow-up Visits.

TABLE 1

Treatment Schedule

| Treatment Week | Number of capsules taken per day | Total Daily Dose |
|---|---|---|
| Treatment Group # 1: ADX-N05 | | |
| Weeks 1-4 | 1 | 150 mg |
| Weeks 5-12 | 2 | 300 mg |
| Treatment Group # 2: Placebo | | |
| Weeks 1-4 | 1 | 0 |
| Weeks 5-12 | 2 | 0 |

Prior to initiating the 12-week treatment period, subjects complete a Screening Phase of up to 28 days, during which time all screening assessments are performed and any current narcolepsy treatments discontinued as well as a Baseline Phase, including an overnight stay at the investigational site, during which time Baseline efficacy and safety assessments are obtained. During the Treatment Phase, subjects return to the investigative site to complete efficacy and safety assessments at the end of Weeks 1, 2, 4, 6, 8, and 12; the Week 4 and Week 12 Visits also include an overnight stay at the investigational site. Subjects take their final dose of study drug at the Week 12 Visit prior to Week 12 Visit assessments. Subjects return at the end of Week 13 for Follow up assessments and unless there are any outstanding safety issues that require follow-up, subjects are discharged from the study at that visit.

Exploratory endpoints of the study are: (1) change from Baseline in the median number of cataplectic attacks per week for the subset of subjects with cataplexy for ADX-N05 vs. placebo at Week 4 and at last assessment; and (2) primary and secondary efficacy endpoints for the subset of subjects with cataplexy. Patients keep a cataplexy diary to track the number of episodes. The change from Baseline in median number of cataplectic attacks per week for the subset of subjects with cataplexy for ADX-N05 vs. placebo at Week 4 and at last available assessment is calculated for the subset of subjects with cataplexy in each of the treatment groups. A Wilcoxon rank-sum test is used to compare the two treatment groups. The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

We claim:

1. A method of treating cataplexy in a subject in need thereof, comprising administering to the subject a therapeutically effective amount of a compound of Formula (I):

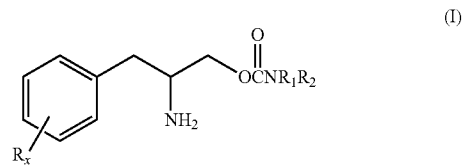

or a pharmaceutically acceptable salt or ester thereof;
wherein R is a member selected from the group consisting of hydrogen, lower alkyl of 1 to 4 carbon atoms, halogen selected from F, Cl, Br and I, alkoxy containing 1 to 3 carbon atoms, nitro, hydroxy, trifluoromethyl, and thioalkoxy containing 1 to 3 carbon atoms;
x is an integer of 0 to 3, with the proviso that R may be the same or different when x is 2 or 3;
$R_1$ and $R_2$ are independently selected from the group consisting of hydrogen, lower alkyl of 1 to 4 carbon atoms, aryl, arylalkyl, cycloalkyl of 3 to 7 carbon atoms; or
$R_1$ and $R_2$ can be joined to form a 5 to 7-membered heterocycle substituted with a member selected from the group consisting of hydrogen, alkyl, and aryl groups, wherein the heterocycle can comprise 1 to 2 nitrogen atoms and 0 to 1 oxygen atom, wherein the nitrogen atoms are not directly connected with each other or with the oxygen atom.

2. The method of claim 1, wherein x=0.

3. The method of claim 1, wherein the compound of Formula I is an enantiomer of Formula I substantially free of other enantiomers or an enantiomeric mixture wherein one enantiomer of Formula I predominates.

4. The method of claim 3, wherein the enantiomer of Formula I predominates to the extent of about 98% or greater.

5. The method of claim 1, wherein the cataplexy is associated with narcolepsy.

6. The method of claim 1, wherein the cataplexy is secondary to a condition that lowers hypocretin levels in the subject.

7. The method of claim 6, wherein the condition is selected from the group consisting of brain tumor, astrocytomas, glioblastoma, glioma, subependynoma, craniopharyngioma, arterio-venous malformations, ischemic events, multiple sclerosis, head injury, brain surgery, paraneoplastic syndromes, Neimann-Pick type C disease, and encephalitis.

8. The method of claim 1, wherein the therapeutically effective amount of the compound of Formula I is from about 0.01 mg/kg/dose to about 150 mg/kg/dose.

9. The method of claim 1, wherein the therapeutically effective amount of the compound of Formula I is from about 1 mg/day to about 7000 mg/day.

10. The method of claim 1, wherein the compound of Formula I is administered orally.

11. The method of claim 1, wherein the compound of Formula I is administered in the form of a capsule or tablet.

12. The method of claim 1, wherein the compound of Formula I is administered in the form of a capsule at a dose of about 150 mg to about 300 mg without any excipients.

\* \* \* \* \*

UNITED STATES PATENT AND TRADEMARK OFFICE
CERTIFICATE OF CORRECTION

PATENT NO. : 11,072,579 B2
APPLICATION NO. : 16/359446
DATED : July 27, 2021
INVENTOR(S) : Khayrallah et al.

Page 1 of 1

It is certified that error appears in the above-identified patent and that said Letters Patent is hereby corrected as shown below:

On the Title Page

(71) Applicants:
Please correct "Jazz Pharmaceuticals International Ill Limited, Hamilton (BM)"
To read -- Jazz Pharmaceuticals Ireland Limited, Dublin (IE) --

In the Specification

Column 1, Line 7:
Please correct "2017which"
To read -- 2017, which --

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*